United States Patent [19]

Kaufhold

[11] Patent Number: 5,118,834
[45] Date of Patent: Jun. 2, 1992

[54] PROCESS FOR THE PREPARATION OF BUTYL 2-PHENYLCYCLOPROPANECARBOXY-LATES

[75] Inventor: Manfred Kaufhold, Marl, Fed. Rep. of Germany

[73] Assignee: Huels Aktiengesellschaft, Marl, Fed. Rep. of Germany

[21] Appl. No.: 755,180

[22] Filed: Sep. 5, 1991

[30] Foreign Application Priority Data

Dec. 22, 1990 [DE] Fed. Rep. of Germany ....... 4041540

[51] Int. Cl.$^5$ .............................................. C07C 69/76
[52] U.S. Cl. .................................................. 560/102
[58] Field of Search ......................................... 560/102

[56] References Cited

U.S. PATENT DOCUMENTS

| | | | |
|---|---|---|---|
| 4,012,430 | 3/1977 | Verbrugge | 560/102 |
| 4,220,591 | 9/1980 | Holan | 560/102 |
| 4,264,606 | 4/1981 | Ozawa | 560/102 |
| 4,360,690 | 11/1982 | Fuchs et al. | 560/102 |
| 4,418,202 | 11/1983 | Fayler | 560/102 |

FOREIGN PATENT DOCUMENTS 3722957 1/1989 Fed. Rep. of Germany.
6092249 7/1981 Japan.

OTHER PUBLICATIONS

Arenal, I. et al., Synthesis (8) 773-5 1985.
Gaudemar-Bardone, F. et al., Synthesis, (12) 1130-3 1987.

Primary Examiner—Paul J. Killos
Attorney, Agent, or Firm—Oblon, Spivak, McClelland, Maier & Neustadt

[57] ABSTRACT

Butyl 2-phenylcyclopropanecarboxylate is prepared by reacting 5-phenylbutyrolactone in a butanol solvent in the presence of HCl in a molar ratio of 5-phenylbutyrolactone to butanol of 1:1 to 1:5 in the absence of a catalyst at 0° to 50° C., thereby producing 4-chloro-4-phenylbutanoate, removing butanol and water from the ester product by distillation, and cyclizing the 4-chloro-4-phenylbutanoate without purification in a solution of a sodium butoxide in the corresponding butanol at 50° to 150° C. and at a molar ratio of alcoholate to chlorine compound of 1:1 to 3:1.

5 Claims, No Drawings

PROCESS FOR THE PREPARATION OF BUTYL 2-PHENYLCYCLOPROPANECARBOXYLATES

BACKGROUND OF THE INVENTION

1. Field of the Invention

The invention relates to a process for the preparation of butyl 2-phenylcyclopropanecarboxylates (=BPCP) of the formula (1) and the corresponding amide (2) by reaction of 5-phenylbutyrolactone (3) with hydrogen chloride and a butyl alcohol to give a 4-chloro-4-phenylbutanoic ester (=CPBE) of the formula (4) and subsequent cyclization with an alcoholate to give (1) and reaction with ammonia to give amide (2).

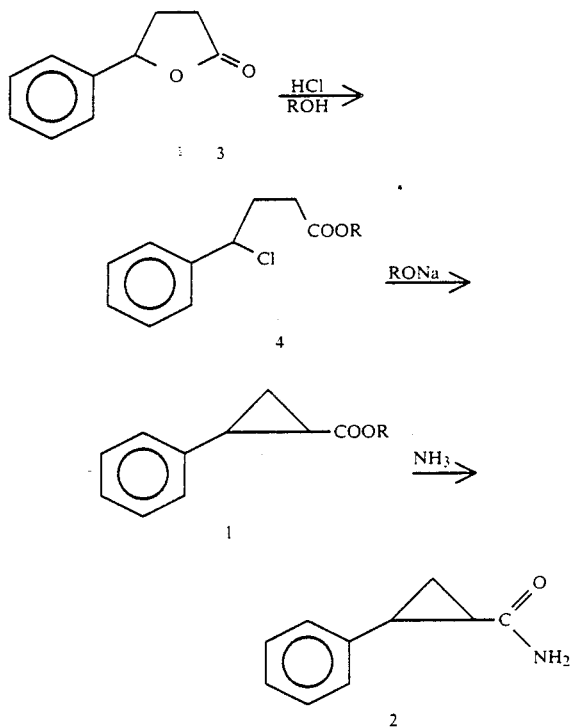

2. Description of the Background

Syntheses of 4-chloro-4-phenylbutanoic esters and 2-phenylcyclopropanecarboxylic esters starting from 5-phenylbutyrolactone, which is easily accessible by reaction of acrylic acid with benzyl alcohol, are known from the literature.

Thus, as early as 1960, U. and S. Julia and B. Bémont described two syntheses of ethyl 4-chloro-4-phenylbutanoate and ethyl 2-phenylcyclopropanecarboxylate starting from 5-phenylbutyrolactone (*Bull. Soc. Chim. France* 1960, 304–12). In method A, a solution of (3) is dissolved in ethanol, saturated with hydrogen chloride, allowed to stand for 48 hours, poured onto ice water, extracted with ether and worked up by distillation. The yield is only 66%.

In method B, (3) is first reacted with thionyl chloride, the reaction product is added to a solution of hydrogen chloride in ethanol and worked up by distillation. A very high yield of 97% is obtained. The 2nd step, the ring formation, is carried out using sodium tert.-amylate in benzene over a period of 35 hours. The workup is carried out similarly to that in the first step by treatment with ice water, extraction with ether and washing of the ether solutions. Workup by distillation gives the desired product in 77% yield.

These procedures are expensive and lead to many waste products. The use of, for example, thionyl chloride is unfavorable in terms of costs when compared with the use of hydrogen chloride. The use of solid sodium amylate in benzene requires additional costs during preparation of this mixture and workup after the reaction.

For analogous ring closure reactions, R. Lantzsch (*Synthesis* 1982, 11, 955–956) suggested a cyclization process which operates with the easily handlable aqueous potassium hydroxide solution. However, the disadvantage of this method is the extremely high dilution caused by the required solvent and the use of very large amounts of phase transfer catalysts, which, in terms of weight, amount to more than one-fourth of the weight of the feed material, i.e., the compound analogous to 4. This causes waste water problems and high costs of the feed materials, which by far outweigh the advantages of potassium hydroxide solution.

All the known processes require expensive chemicals, are technically very complex and time-consuming and lead to problems in waste disposal. A process is therefore desirable in which 5-phenylbutyrolactone is converted into a 4-chloro-4-phenylbutanoic ester with hydrogen chloride and an alcohol in a one-pot process and this ester is cyclized without pressure in conventional reactors. The 2-phenylcyclopropanecarboxylic ester obtained can be converted, for example, catalytically to the amide with ammonia.

Such a process, by which butyl 2-phenylcyclopropanecarboxylate can be prepared from 5-phenylbutyrolactone and, if desired, 2-phenylcyclopropanecarboxyamide can be prepared from this ester in a technically simple manner and without the use of expensive reagents, is of great interest, since these products are important raw materials for pharmaceutical products.

SUMMARY OF THE INVENTION

Accordingly, one object of the present invention is to provide a method of preparing 2-phenylcyclopropanecarboxylate in improved yield and quality.

Briefly, this object and other objects of the present invention as hereinafter will become more readily apparent can be attained by a method of preparing butyl 2-phenylcyclopropanecarboxylate by reacting 5-phenylbutyrolactone in a butanol solvent in the presence of HCl in a molar ratio of 5-phenylbutyrolactone to butanol of 1:1 to 1:5 in the absence of a catalyst at 0° C. to 50° C., thereby producing 4-chloro-4-phenylbutanoate; removing butanol and water from the ester product by distillation; and cyclizing the 4-chloro-4-phenylbutanoate without purification in a solution of a sodium butoxide in the corresponding butanol at 50° C. to 150° C. and at a molar ratio of alcoholate to chlorine compound of 1:1 to 3:1.

DETAILED DESCRIPTION OF THE PREFERRED EMBODIMENTS

It has now been discovered that in the first reaction step, the reaction of 5-phenylbutyrolactone with hydrogen chloride and butanol can be carried out in a very short time and in a very simple manner by working at room temperature, rapidly removing the heat of reaction and then distilling off excess butanol at low temperatures. Suitable butanols are n-butanol and isobutanol.

The reaction takes place at 0° C. to 50° C., preferably at 10° C. to 20° C., in the absence of a catalyst.

The cyclization of isobutyl 4-chloro-4-phenylbutanoate in the second reaction step proceeds surprisingly smoothly at atmospheric pressure and very high yields of more than 95% by adding the chlorine compound at relatively high temperatures to a solution of a sodium alcoholate in the corresponding alcohol having 4 or more C atoms. This leads to unusually short reaction times of, for example, 1 hour. Longer reaction times reduce the yields.

This finding that high temperatures and short times are favorable is in contrast to the disclosures of the above-mentioned literature references, which carry out the cyclization reactions at relatively low temperatures and then require longer reaction times. Thus, R. Lantzsch selects reaction temperatures of 35° C. to 40° C. and requires 3 hours for the reaction. The reference expressly mentions the risk of elimination of hydrogen chloride in a side reaction, in particular if strong bases and the compound investigated are used, which are tertiary chlorine compounds, which, as is known, are particularly unstable compared with secondary and primary compounds.

The chlorine compound (4) present is particularly unstable, since it is additionally activated by the benzene ring and forms a stable styrene derivative upon elimination of hydrogen chloride:

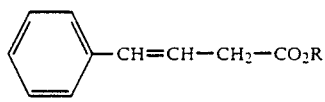

That is why the finding is particularly surprising and novel.

The alcoholates or alcohols used are butanols, in particular n-butanol and isobutanol. Although it is possible to use alcohols having 5 to 20 C atoms or the corresponding alcoholates, they do not result in the advantages of the invention.

The use of sodium n- or iso-butoxide solution in the corresponding butanol is particularly favorable in terms of costs, because it can be prepared in a simple manner from sodium hydroxide solution and n-butanol or by means of sodium methoxide, without the necessity of processing an air-sensitive solid. Furthermore, it has surprisingly been found that the butyl 4-chloro-4-phenylbutanoate used does not have to be purified by distillation but can be used in the form of the crude product. This is a great advantage with respect to yield and production costs, given its low thermal stability.

In practice, the individual steps are carried out, for example, in the following manner:

Butyl 4-chloro-4-phenylbutanoate is prepared without using a catalyst. 5-Phenylbutyrolactone and n- or iso-butanol are initially introduced in a molar ratio of 1:1 to 1:5, preferably 1:2 to 1:3, and hydrogen chloride is introduced at room temperature. Heat is evolved, which is removed. Hydrogen chloride is introduced at the rate at which the gas is absorbed up to saturation. The reaction temperature is set at 0° C. to 50° C., preferably 10° C. to 20° C. When gas absorption is complete, the major portion of butanol is removed by distillation and the distillation residue is further processed without purification.

Cyclization of butyl 4-chloro-4-phenylbutanoate is carried out at 50° C. to 150° C., preferably 90° C. to 110° C., by initially introducing, for example, a solution of sodium iso-butoxide in isobutanol, adding butyl 4-chloro-4-phenylbutanoate and heating the mixture.

The reaction time must be as short as possible, because otherwise byproducts are increasingly formed.

The molar ratio of alcoholate to butyl 4-chloro-4-phenylbutanoate is 1:1 to 3:1, preferably 1.8:1 to 1.1:1.

The butyl 2-phenylcyclopropanecarboxylate obtained is reacted, for example, in a manner known per se with ammonia to give the amide, which is an important intermediate for preparing pharmaceutical products. The amide is also prepared by using a solution of sodium n- or iso-butoxide in the corresponding butanol as the catalyst, butanol as the solvent and an ammonia pressure of, for example, 12 bar at reaction temperatures of, for example, 120° C. This embodiment is advantageous, since after the reaction the amide precipitates upon cooling in the form of crystals and is recovered in pure form in an extremely simple manner by filtration. The mother liquor can be used again.

Having generally described this invention, a further understanding can be obtained by reference to certain specific examples which are provided herein for purposes of illustration only and are not intended to be limiting unless otherwise specified.

EXAMPLE 1 a

Isobutyl 4-chloro-4-phenylbutanoate (=CPBE) (1st step)

A glass apparatus is used which comprises a four-necked flask equipped with gas inlet tube, stirrer, thermometer, dropping funnel and reflux condenser. To the flask is added 711 g (3.99 mol) of 5-phenylbutyrolactone (91.1% pure) and 741 g (10 mol) of isobutanol.

The feed materials are initially introduced and hydrogen chloride is introduced, while cooling the flask with an ice bath, at the rate at which the gas is absorbed by the solution. The temperatures vary between 10° C. and 20° C. After 3 hours, absorption is complete. The target product content, calculated free of solvent, is 82.8% by GC analysis.

Excess hydrogen chloride and the major portion of isobutanol, 536.5 g, are removed by distillation in a vacuum of 130 to 50 mbar. The distillation residue, 1,079 g, contains 88.2% of CPBE, which corresponds to a yield of 952 g of CPBE=93.6% of theory, relative to the feed material, in addition to 1.3% of isobutanol. This product is further processed without purification.

EXAMPLE 1 b

Isobutyl 2-phenylcyclopropanecarboxylate (=PCPE) (2nd step)

A glass apparatus is used which comprises a three-necked flask equipped with stirrer, thermometer, dropping funnel and a glass column, 0.5 m in length, filled with glass Raschig rings and fitted with a distillation head. The following ingredients are employed in the reaction:

143 g (0.79 mol) of sodium methoxide solution (30% strength),
196 g (2.6 mol) of isobutanol and
200.5 g (0.69 mol) of CPBE 88.2% pure from step 1.

Isobutanol and sodium methoxide solution are initially introduced, 204 g of a solution of sodium isobutoxide in isobutanol are prepared by distilling off methanol and a small amount of isobutanol. CPBE is then added dropwise at 100° C. over a period of 0.5 hour, and the mixture is stirred at this temperature for another hour. After cooling, the mixture is washed with 175 g of water containing 7.5% of phosphoric acid and washed again with 130 g of an aqueous common salt solution. GC analysis of the organic phase, 251.5 g, calculated with water; 236 g, calculated without water, showed the following composition:

| | |
|---|---|
| isobutanol | 33.1% |
| unknown component | 1.4% |
| cis-PCPE | 2.7% ⎫ |
| trans-PCPE | 59.0% ⎬ 61.7% |
| | 96.2% |

The yield of cis- and trans PCPE formed and calculated therefrom is 146 g=96.7% of theory, relative to the feed material. Workup by distillation in the boiling range from 157° C. to 158° C. at 30 mbar gives the PCPE with a trans content of more than 90%.

EXAMPLES 2 to 5 (2nd step)

The apparatus described in 1b is used and the amounts of feed materials mentioned there are used. The reaction time is limited to 1 hour, and reaction temperatures of 50° C., 70° C., 80° C., 100° C. and 120° C. are chosen. The following relationships between reaction temperature (RT) and yield are obtained:

| RT in °C. | Yield in % |
|---|---|
| 50 | 71 |
| 70 | 75 |
| 80 | 81 |
| 100 | 97 |
| 120 | 90 |

Having now fully described the invention, it will be apparent to one of ordinary skill in the art that many changes and modifications can be made thereto without departing from the spirit or scope of the invention as set forth herein.

What is claimed as new and desired to be secured by letters patent of the United States is:

1. A process for the preparation of butyl 2-phenylcyclopropanecarboxylate, comprising the steps of:
   reacting 5-phenylbutyrolactone in a butanol solvent in the presence of HCl in a molar ratio of 5-phenylbutyrolactone to butanol of 1:1 to 1:5 in the absence of a catalyst at 0° C. to 50° C., thereby producing 4-chloro-4-phenylbutanoate;
   removing butanol and water from the ester product by distillation; and
   cyclizing the 4-chloro-4-phenylbutanoate without purification in a solution of a sodium butoxide in the corresponding butanol at 50° C. to 150° C. and at a molar ratio of alcoholate to chlorine compound of 1:1 to 3:1.

2. The process according to claim 1, wherein, in the first step, 5-phenylbutyrolactone and butanol are reacted in a molar ratio of 1:2 to 1:3.

3. The process according to claim 1 or 2, wherein the reaction of the first step is carried out at 10° C. to 20° C.

4. The process according to claim 1, wherein the second step cyclization is carried out at a molar ratio of alcoholate to butyl 4-chloro-4-phenylbutanoate of 1.8:1 to 1.1:1.

5. The process according to claim 1 or 4, wherein the second step cyclization is carried out at a temperature of 90° C. to 110° C.

* * * * *